United States Patent [19]

Raymond

[11] Patent Number: 5,736,383
[45] Date of Patent: Apr. 7, 1998

[54] **PREPARATION OF *PICHIA METHANOLICA* AUXOTROPHIC MUTANTS**

[75] Inventor: Christopher K. Raymond, Seattle, Wash.

[73] Assignee: ZymoGenetics, Inc., Seattle, Wash.

[21] Appl. No.: 703,808

[22] Filed: Aug. 26, 1996

[51] Int. Cl.$^6$ .............................. C12N 1/16; C12N 15/01
[52] U.S. Cl. ................. 435/255.7; 435/34; 435/172.1; 435/255.5; 935/37
[58] Field of Search .......................... 435/691, 255.5, 435/255.7, 34, 172.1, 37

[56] References Cited

U.S. PATENT DOCUMENTS 4,879,231  11/1989  Stroman et al. ............... 435/172.3

OTHER PUBLICATIONS

American Type Culture Collection. Catalogue of Yeasts: Eighteenth edition, 1990. Jong, SC and Edwards, MJ, eds. Rockville, MD, 1990.

Janatova, I. Antoine van Leeuwenhoek. 62: 167–171, 1992.

Gould et al., *Yeast* 8: 613–628, 1992.

Piredda et al., *Yeast* 10: 1601–1612, 1994.

Hiep et al., *Yeast* 9: 1251–1258, 1993.

Strathem (ed.) et al., *The Molecular Biology of the Yeast Saccharomyces:* 271–279, 1982.

Hiep et al., *Yeast* 9: 1189–1197, 1993.

*Primary Examiner*—David Saunders
*Assistant Examiner*—F. Pierre VanderVegt
*Attorney, Agent, or Firm*—Gary E. Parker

[57] ABSTRACT

Methods for preparing *Pichia methanolica* cells having auxotrophic mutations are disclosed. The methods comprise the steps of (a) exposing *P. methanolica* cells to mutagenizing conditions, (b) culturing the cells from step (a) in a rich medium to allow mutations to become established and replicated in at least a portion of the cells, (c) culturing the cells from step (b) in a culture medium deficient in assimilable nitrogen to deplete cellular nitrogen stores, (d) culturing the cells from step (c) in a defined culture medium comprising an inorganic nitrogen source and an amount of nystatin sufficient to kill growing *P. methanolica* cells to select for cells having a deficiency in a nutritional gene; and (e) culturing the selected cells from step (d) in a rich culture medium.

8 Claims, 3 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3077 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
CAGCTGCTCT   GCTCCTTGAT   TCGTAATTAA   TGTTATCCTT   TTACTTTGAA   CTCTTGTCGG    60

TCCCCAACAG   GGATTCCAAT   CGGTGCTCAG   CGGGATTTCC   CATGAGGTTT   TTGACAACTT   120

TATTGATGCT   GCAAAAACTT   TTTTAGCCGG   GTTTAAGTAA   CTGGGCAATA   TTTCCAAAGG   180

CTGTGGGCGT   TCCACACTCC   TTGCTTTTCA   TAATCTCTGT   GTATTGTTTT   ATTCGCATTT   240

TGATTCTCTT   ATTACCAGTT   ATGTAGAAAG   ATCGGCAAAC   AAAATATCAA   CTTTTATCTT   300

GAACGCTGAC   CCACGGTTTC   AAATAACTAT   CAGAACTCTA   TAGCTATAGG   GGAAGTTTAC   360

TGCTTGCTTA   AAGCGGCTAA   AAAGTGTTTG   GCAAATTAAA   AAAGCTGTGA   CAAGTAGGAA   420

CTCCTGTAAA   GGGCCGATTC   GACTTCGAAA   GAGCCTAAAA   ACAGTGACTA   TTGGTGACGG   480

AAAATTGCTA   AAGGAGTACT   AGGGCTGTAG   TAATAAATAA   TGGAACAGTG   GTACAACAAT   540

AAAAGAATGA   CGCTGTATGT   CGTAGCCTGC   ACGAGTAGCT   CAGTGGTAGA   GCAGCAGATT   600

GCAAATCTGT   TGGTCACCGG   TTCGATCCGG   TCTCGGGCTT   CCTTTTTTGC   TTTTTCGATA   660
```

-continued

| | | | | | |
|---|---|---|---|---|---|
| TTTGCGGGTA | GGAAGCAAGG | TCTAGTTTTC | GTCGTTTCGG | ATGGTTTACG | AAAGTATCAG | 720 |
| CCATGAGTGT | TTCCCTCTGG | CTACCTAATA | TATTTATTGA | TCGGTCTCTC | ATGTGAATGT | 780 |
| TTCTTTCCAA | GTTCGGCTTT | CAGCTCGTAA | ATGTGCAAGA | AATATTTGAC | TCCAGCGACC | 840 |
| TTTCAGAGTC | AAATTAATTT | TCGCTAACAA | TTTGTGTTTT | TCTGGAGAAA | CCTAAAGATT | 900 |
| TAACTGATAA | GTCGAATCAA | CATCTTTAAA | TCCTTTAGTT | AAGATCTCTG | CAGCGGCCAG | 960 |
| TATTAACCAA | TAGCATATTC | ACAGGCATCA | CATCGGAACA | TTCAGAATGG | ACTCGCAAAC | 1020 |
| TGTCGGGATT | TTAGGTGGTG | GCCAACTTGG | TCGTATGATC | GTTGAAGCTG | CACACAGATT | 1080 |
| GAATATCAAA | ACTGTGATTC | TCGAAAATGG | AGACCAGGCT | CCAGCAAAGC | AAATCAACGC | 1140 |
| TTTAGATGAC | CATATTGACG | GCTCATTCAA | TGATCCAAAA | GCAATTGCCG | AATTGGCTGC | 1200 |
| CAAGTGTGAT | GTTTTAACCG | TTGAGATTGA | ACATGTTGAC | ACTGATGCGT | TGGTTGAAGT | 1260 |
| TCAAAAGGCA | ACTGGCATCA | AAATCTTCCC | ATCACCAGAA | ACTATTTCAT | TGATCAAAGA | 1320 |
| TAAATACTTG | CAAAAGAGC | ATTTGATTAA | GAATGGCATT | GCTGTTGCCG | AATCTTGTAG | 1380 |
| TGTTGAAAGT | AGCGCAGCAT | CTTTAGAAGA | AGTTGGTGCC | AAATACGGCT | TCCCATACAT | 1440 |
| GCTAAAATCT | AGAACAATGG | CCTATGACGG | AAGAGGTAAT | TTGTTGTCA | AAGACAAGTC | 1500 |
| ATATATACCT | GAAGCTTTGA | AAGTTTTAGA | TGACAGGCCG | TTATACGCCG | AGAAATGGGC | 1560 |
| TCCATTTTCA | AAGGAGTTAG | CTGTTATGGT | TGTGAGATCA | ATCGATGGCC | AAGTTTATTC | 1620 |
| CTACCCAACT | GTTGAAACCA | TCCACCAAAA | CAACATCTGT | CACACTGTCT | TTGCTCCAGC | 1680 |
| TAGAGTTAAC | GATACTGTCC | AAAAGAAGGC | CCAAATTTTG | GCTGACAACG | CTGTCAAATC | 1740 |
| TTTCCCAGGT | GCTGGTATCT | TTGGTGTTGA | AATGTTTTA | TTACAAAATG | GTGACTTATT | 1800 |
| AGTCAACGAA | ATTGCCCCAA | GACCTCACAA | TTCTGGTCAC | TATACCATCG | ACGCTTGTGT | 1860 |
| CACCTCGCAA | TTTGAAGCTC | ATGTTAGGGC | CATTACTGGT | CTACCCATGC | CGAAGAACTT | 1920 |
| CACTTGTTTG | TCGACTCCAT | CTACCCAAGC | TATTATGTTG | AACGTTTTAG | GTGGCGATGA | 1980 |
| GCAAAACGGT | GAGTTCAAGA | TGTGTAAAAG | AGCACTAGAA | ACTCCTCATG | CTTCTGTTTA | 2040 |
| CTTATACGGT | AAGACTACAA | GACCAGGCAG | AAAAATGGGT | CACATTAATA | TAGTTTCTCA | 2100 |
| ATCAATGACT | GACTGTGAGC | GTAGATTACA | TTACATAGAA | GGTACGACTA | ACAGCATCCC | 2160 |
| TCTCGAAGAA | CAGTACACTA | CAGATTCCAT | TCCGGGCACT | TCAAGCAAGC | CATTAGTCGG | 2220 |
| TGTCATCATG | GGTTCCGATT | CGGACCTACC | AGTCATGTCT | CTAGGTTGTA | ATATATTGAA | 2280 |
| GCAATTTAAC | GTTCCATTTG | AAGTCACTAT | CGTTTCCGCT | CATAGAACCC | CACAAAGAAT | 2340 |
| GGCCAAGTAT | GCCATTGATG | CTCCAAAGAG | AGGGTTGAAG | TGCATCATTG | CTGGTGCTGG | 2400 |
| TGGTGCCGCT | CATTTACCGG | GAATGGTTGC | GGCGATGACG | CCGCTGCCTG | TTATTGGTGT | 2460 |
| CCCTGTTAAA | GGCTCTACTT | TGGATGGTGT | TGATTCACTA | CACTCCATCG | TTCAAATGCC | 2520 |
| AAGAGGTATT | CCTGTTGCTA | CTGTGGCTAT | TAACAATGCT | ACTAACGCTG | CCTTGCTAGC | 2580 |
| TATCACAATC | TTAGGTGCCG | GCGATCCAAA | TACTTGTCTG | CAATGGAAGT | TTATATGAAC | 2640 |
| AATATGGAAA | ATGAAGTTTT | GGGCAAGGCT | GAAAAATTGG | AAAATGGTGG | ATATGAAGAA | 2700 |
| TACTTGAGTA | CATACAAGAA | GTAGAACCTT | TTATATTTGA | TATAGTACTT | ACTCAAAGTC | 2760 |
| TTAATTGTTC | TAACTGTTAA | TTTCTGCTTT | GCATTTCTGA | AAAGTTTAAG | ACAAGAAATC | 2820 |
| TTGAAATTTC | TAGTTGCTCG | TAAGAGGAAA | CTTGCATTCA | AATAACATTA | ACAATAAATG | 2880 |
| ACAATAATAT | ATTATTTCAA | CACTGCTATA | TGGTAGTTTT | ATAGGTTTGG | TTAGGATTTG | 2940 |
| AGATATTGCT | AGCGCTTATC | ATTATCCTTA | ATTGTTCATC | GACGCAAATC | GACGCATTTC | 3000 |
| CACAAAAATT | TTCCGAACCT | GTTTTTCACT | TCTCCAGATC | TTGGTTTAGT | ATAGCTTTTG | 3060 |

ACACCTAATA CCTGCAG                                                                                          3077

( 2 ) INFORMATION FOR SEQ ID NO:2:

( i ) SEQUENCE CHARACTERISTICS:
        ( A ) LENGTH: 3386 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

```
GAATTCCTGC AGCCCGGGGG ATCGGGTAGT GGAATGCACG GTTATACCCA CTCCAAATAA    60
AAGTGTAGTA GCCGGACTGA AAGGTTTTAG GAGTCTGTTT GTTGTTCAT  GTGCATCATT   120
CCCTAATCTG TTAACAGTCT CGGAGTATAC AAAAAAGTAA GTCAAATATC AAGGTGGCCG   180
GGGGCAGCAT CGAGACTCGA GATGGTACAT ACTTAAAAGC TGCCATATTG AGGAACTTCA   240
AAGTTTTATC TGTTTTTAGA ATTAAAAGAC GATTGTTGTA ACAAAACGTT GTGCCTACAT   300
AAACTCAAAT TAATGGAAAT AGCCTGTTTT GAAAAATACA CCTTCTTAAG TACTGACAAA   360
GTTTTGTTAA ATGACTATCG AACAAGCCAT GAAATAGCAC ATTTCTGCCA GTCACTTTTA   420
ACACTTTCCT GCTTGCTGGT TGACTCTCCT CATACAAACA CCCAAAAGGG AAACTTTCAG   480
TGTGGGACA  CTTGACATCT CACATGCACC CCAGATTAAT TTCCCCAGAC GATGCGGAGA   540
CAAGACAAAA CAACCCTTTG TCCTGCTCTT TTCTTTCTCA CACCGCGTGG GTGTGTGCGC   600
AGGCAGGCAG GCAGGCAGCG GGCTGCCTGC CATCTCTAAT CGCTGCTCCT CCCCCCTGGC   660
TTCAAATAAC AGCCTGCTGC TATCTGTGAC CAGATTGGGA CACCCCCTC  CCCTCCGAAT   720
GATCCATCAC CTTTTGTCGT ACTCCGACAA TGATCCTTCC CTGTCATCTT CTGGCAATCA   780
GCTCCTTCAA TAATTAAATC AAATAAGCAT AAATAGTAAA ATCGCATACA AACGTCATGA   840
AAAGTTTTAT CTCTATGGCC AACGGATAGT CTATCTGCTT AATTCCATCC ACTTTGGGAA   900
CCGCTCTCTC TTTACCCCAG ATTCTCAAAG CTAATATCTG CCCCTTGTCT ATTGTCCTTT   960
CTCCGTGTAC AAGCGGAGCT TTGCCTCCC  ATCCTCTTGC TTTGTTTCGG TTATTTTTTT  1020
TTCTTTTGAA ACTCTTGGTC AAATCAAATC AAACAAAACC AAACCTTCTA TTCCATCAGA  1080
TCAACCTTGT TCAACATTCT ATAAATCGAT ATAAATATAA CCTTATCCCT CCCTTGTTTT  1140
TTACCAATTA ATCAATCTTC AAATTTCAAA TATTTCTAC  TTGCTTTATT ACTCAGTATT  1200
AACATTTGTT TAAACCAACT ATAACTTTTA ACTGGCTTTA GAAGTTTTAT TTAACATCAG  1260
TTTCAATTTA CATCTTTATT TATTAACGAA ATCTTTACGA ATTAACTCAA TCAAAACTTT  1320
TACGAAAAAA AAATCTTACT ATTAATTTCT CAAAATGGCT ATTCCAGATG AATTTGATAT  1380
TATTGTTGTC GGTGGTGGTT CCACCGGTTG TGCTCTTGCT GGTAGATTAG GTAACTTGGA  1440
CGAAAACGTC ACAGTTGCTT TAATCGAAGG TGGTGAAAAC AACATCAACA ACCATGGGT   1500
TTACTTACCA GGTGTTTATC CAAGAAACAT GAGATTAGAC TCAAAGACTG CTACTTTTA   1560
CTCTTCAAGA CCATCACCAC ACTTGAACGG TAGAAGAGCT ATTGTTCCAT GTGCTAACAT  1620
CTTGGGTGGT GGTTCTTCCA TCAACTTCTT GATGTACACC AGAGCCTCTG CCTCCGATTA  1680
CGATGATTGG GAATCTGAAG GTTGGACTAC CGATGAATTA TTACCACTAA TGAAGAAGAT  1740
```

```
TGAAACTTAT CAAAGACCAT GTAACAACAG AGAATTGCAC GGTTTCGATG GTCCAATTAA    1800
GGTTTCATTT GGTAACTATA CTTATCCAAA CGGTCAAGAT TTCATTAGAG CTGCCGAATC    1860
TCAAGGTATT CCATTGTTG ATGATGCTGA AGATTTGAAA TGTTCCACG GTGCTGAGCA      1920
CTGGTTGAAG TGGATCAACA GAGACTTAGG TAGAAGATCC GATTCTGCTC ATGCTTACAT    1980
TCACCCAACC ATGAGAAACA AGCAAAACTT GTTCTTGATT ACTTCCACCA AGTGTGAAAA    2040
GATTATCATT GAAAACGGTG TTGCTACTGG TGTTAAGACT GTTCCAATGA AGCCAACTGG    2100
TTCTCCAAAG ACCCAAGTTG CTAGAACTTT CAAGGCTAGA AAGCAAATTA TTGTTTCTTG    2160
TGGTACTATC TCATCACCAT TAGTTTTGCA AAGATCTGGT ATCGGTTCCG CTCACAAGTT    2220
GAGACAAGTT GGTATTAAAC CAATTGTTGA CTTACCAGGT GTTGGTATGA ACTTCCAAGA    2280
TCACTACTGT TTCTTCACTC CATACCATGT CAAGCCAGAT ACTCCATCAT TCGATGACTT    2340
TGTTAGAGGT GATAAAGCTG TTCAAAAATC TGCTTCGAC CAATGGTATG CTAACAAGGA     2400
TGGTCCATTA ACCACTAATG GTATTGAGGC AGGTGTTAAG ATTAGACCAA CTGAAGAAGA    2460
ATTAGCCACT GCTGATGACG AATTCAGAGC TGCTTATGAT GACTACTTTG GTAACAAGCC    2520
AGATAAGCCA TTAATGCACT ACTCTCTAAT TTCTGGTTTC TTTGGTGACC ACACCAAGAT    2580
TCCAAACGGT AAGTACATGT GCATGTTCCA CTTCTTGGAA TATCCATTCT CCAGAGGTTT    2640
CGTTCACGTT GTTTCTCCAA ACCCATACGA TGCTCCTGAC TTTGATCCAG GTTTCATGAA    2700
CGATCCAAGA GATATGTGGC CAATGGTTTG GTCTTACAAG AAGTCCAGAG AAACTGCCAG    2760
AAGAATGGAC TGTTTTGCCG GTGAAGTTAC TTCTCACCAC CCACACTACC CATACGACTC    2820
ACCAGCCAGA GCTGCTGACA TGGACTTGGA AACTACTAAA GCTTATGCTG GTCCAGACCA    2880
CTTTACTGCT AACTTGTACC ACGGTTCATG GACTGTTCCA ATTGAAAAGC CAACTCCAAA    2940
GAACGCTGCT CACGTTACTT CTAACCAAGT TGAAAAACAT CGTGACATCG AATACACCAA    3000
GGAGGATGAT GCTGCTATCG AAGATTACAT CAGAGAACAC ACTGAAACCA CATGGCATTG    3060
TCTTGGTACT TGTTCAATGG CTCCAAGAGA AGGTTCTAAG GTTGTCCCAA CTGGTGGTGT    3120
TGTTGACTCC AGATTAAACG TTTACGGTGT TGAAAAGTTG AAGGTTGCTG ATTTATCAAT    3180
TTGCCCAGAT AATGTTGGTT GTAACACTTA CTCTACTGCT TTGTTAATCG GTGAAAAGGC    3240
TTCTACCTTA GTTGCTGAAG ACTTGGGCTA CTCTGGTGAT GCTTTGAAGA TGACTGTTCC    3300
AAACTTCAAA TTGGGTACTT ATGAAGAAGC TGGTCTAGCT AGATTCTAGG GCTGCCTGTT    3360
TGGATATTTT TATAATTTTT GAGAGT                                         3386
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
TGATCACCTA GGACTAGTGA CAAGTAGGAA CTCCTGTA                             38
```

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAGCTGCCTA GGACTAGTTT CCTCTTACGA GCAACTAGA                                        39

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGGTTGAAGT GGATCAA                                                                17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GTGTGGTCAC CGAAGAA                                                                17

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC9885

( x i ) SEQUENCE DESCRIPTION: SEQ ID NO:7:

GTTGTTCCTT CCAAACCATT GAAC                                                        24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC9883

( x i ) SEQUENCE DESCRIPTION: SEQ ID NO:8:

AAAGTAAGAA GCGTAGCCTA GTTG                                                        24

( 2 ) INFORMATION FOR SEQ ID NO:9:

( i ) SEQUENCE CHARACTERISTICS:
        ( A ) LENGTH: 329 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

GACCATGATT ACGCCAAGCG CGCAATTAAC CCTCACTAAA GGGAACAAAA GCTGGGTACC                  60

GGGCCCCCCC TCGAGGTCGA CGGTATCGAT AAGCTTTATT ATAACATTAA TATACTATTT                  120

TATAACAGGA TTGAAAATTA TATTTATCTA TCTAAAACTA AAATTCAAAA TGGCTATTCC                  180

TGAAGAATTC GATATCATTG TTGTCGGTGG TGGTTCTGCC GGCTGTCCTA CTGCTGGTAG                  240

```
ATTGGCTAAC  TTAGACCCAA  ATTTAACTGT  TGCTTTAATC  GAAGCTGGTG  AAAACAACAT        300

TAACAACCCA  TGGGTCTACT  TACCAGGCG                                             329
```

PREPARATION OF *PICHIA METHANOLICA* AUXOTROPHIC MUTANTS

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, Hansenula, Pichia, Candida, and Torulopsis. These genera are somewhat artificial, having been based on cell morphology and growth characteristics, and do not reflect close genetic relationships (Billon-Grand, *Mycotaxon* 35:201–204, 1989; Kurtzman, *Mycologia* 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems. Some methylotrophic yeasts have been shown to grow rapidly to high biomass on minimal defined media. Certain genes of methylotrophic yeasts are tightly regulated and highly expressed under induced or de-repressed conditions, suggesting that promoters of these genes might be useful for producing polypeptides of commercial value. See, for example, Faber et al., *Yeast* 11:1331, 1995; Romanos et al., *Yeast* 8:423, 1992; and Cregg et al., *Bio/Technology* 11:905, 1993.

Development of methylotrophic yeasts as hosts for use in recombinant production systems has been slow, due in part to a lack of suitable materials (e.g., promoters, selectable markers, and mutant host cells) and methods (e.g., transformation techniques). The most highly developed methylotrophic host systems utilize *Pichia pastoris* and *Hansenula polymorpha* (Faber et al., *Curr. Genet.* 25:305–310, 1994; Cregg et al., ibid.; Romanos et al., ibid.; U.S. Pat. Nos. 4,855,242; 4,857,467; 4,879,231; and 4,929,555).

There remains a need in the art for methods of transforming additional species of methylotrophic yeasts and for using the transformed cells to produce polypeptides of economic importance, including industrial enzymes and pharmaceutical proteins. The present invention provides compositions and methods useful in these processes as well as other, related advantages.

SUMMARY OF THE INVENTION

The present invention provides methods for preparing *Pichia methanolica* cells having an auxotrophic mutation. The methods comprise the steps of (a) exposing *P. methanolica* cells to mutagenizing conditions; (b) culturing the cells from step (a) in a rich medium to allow mutations to become established and replicated in at least a portion of the cells; (c) culturing the cells from step (b) in a culture medium deficient in assimilable nitrogen to deplete cellular nitrogen stores; (d) culturing the cells from step (c) in a defined culture medium comprising an inorganic nitrogen source and an amount of nystatin sufficient to kill growing *P. methanolica* cells to select for cells having a deficiency in a nutritional gene; and (e) culturing the selected cells from step (d) in a rich culture medium. Within one embodiment of the invention, the selected cells from step (e) are replica plated to a defined medium and cultured to confirm the presence of an auxotrophic mutation. Within another embodiment, the selected cells are auxotrophic for adenine. Within a related embodiment, the selected cells are deficient in phosphoribosyl-5-aminoimidazole carboxylase. Within additional embodiments the mutagenizing conditions comprise exposure to ultraviolet light or exposure to a chemical mutagen. Within a further embodiment, the inorganic nitrogen source comprises ammonium ions.

These and other aspects of the invention will become evident upon reference to the following detailed description and the attached drawings.

DETAILED DESCRIPTION OF THE INVENTION

Figure 1:
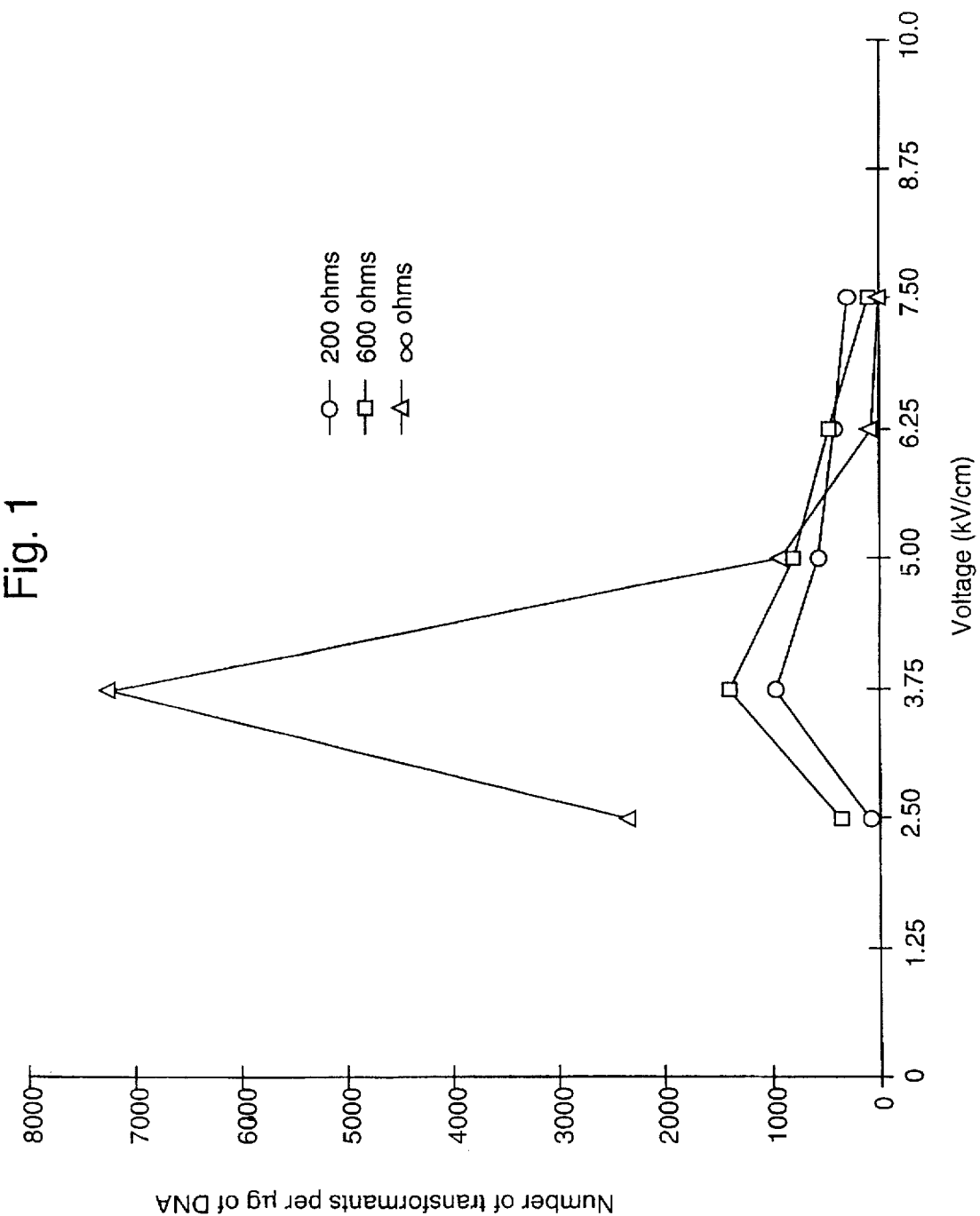
FIG. 1 illustrates the effects of field strength and pulse duration on electroporation efficiency of *P. methanolica*.

Prior to setting forth the invention in more detail, it will be useful to define certain terms used herein:

A "DNA construct" is a DNA molecule, either single- or double-stranded, that has been modified through human intervention to contain segments of DNA combined and juxtaposed in an arrangement not existing in nature.

"Early log phase growth" is that phase of cellular growth in culture when the cell concentration is from $2 \times 10^6$ cells/ml to $8 \times 10^6$ cells/ml.

"Heterologous DNA" refers to a DNA molecule, or a population of DNA molecules, that does not exist naturally within a given host cell. DNA molecules heterologous to a particular host cell may contain DNA derived from the host cell species so long as that host DNA is combined with non-host DNA. For example, a DNA molecule containing a non-host DNA segment encoding a polypeptide operably linked to a host DNA segment comprising a transcription promoter is considered to be a heterologous DNA molecule.

A "higher eukaryotic" organism is a multicellular eukaryotic organism. The term encompasses both plants and animals.

"Integrative transformants" are cells into which has been introduced heterologous DNA, wherein the heterologous DNA has become integrated into the genomic DNA of the cells.

"Linear DNA" denotes DNA molecules having free 5' and 3' ends, that is non-circular DNA molecules. Linear DNA can be prepared from closed circular DNA molecules, such as plasmids, by enzymatic digestion or physical disruption.

The term "operably linked" indicates that DNA segments are arranged so that they function in concert for their intended purposes, e.g., transcription initiates in the promoter and proceeds through the coding segment to the terminator.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. These promoter elements include RNA polymerase binding sites; TATA sequences; CAAT sequences; differentiation-specific elements (DSEs; McGehee et al., *Mol. Endocrinol.* 7:551–560, 1993); cyclic AMP response elements (CREs); serum response elements (SREs; Treisman, *Seminars in Cancer Biol.* 1:47–58, 1990); glucocorticoid response elements (GREs); and binding sites for other transcription factors, such as CRE/ATF (O'Reilly et al., *J. Biol. Chem.* 267:19938–19943, 1992), AP2 (Ye et al., *J. Biol. Chem.* 269:25728–25734, 1994), SP1, cAMP response element binding protein (CREB; Loeken, *Gene Expr.* 3:253–264, 1993) and octamer factors. See, in general, Watson et al., eds., *Molecular Biology of the Gene*, 4th ed., The Benjamin/Cummings Publishing Company, Inc., Menlo Park, Calif., 1987; and Lemaigre and Rousseau, *Biochem. J.* 303:1–14, 1994.

A "repressing carbon source" is a metabolizable, carbon-containing compound that, when not limited, suppresses the expression in an organism of genes required for the catabolism of other carbon sources. By "limited" is meant that the carbon source is unavailable or becomes available at such a rate that it is immediately consumed and therefore the prevailing concentration of that carbon source in an organism's environment is effectively zero. Repressing carbon sources that can be used within the present invention include hexoses and ethanol. Glucose is particularly preferred.

"Rich" culture media are those culture media that are based on complex sources of nutrients, typically cell or tissue extracts or protein hydrolysates. Rich media will vary in composition from batch to batch due to variations in the composition of the nutrient sources.

As noted above, the present invention provides methods for preparing *Pichia methanolica* cells having an auxotrophic mutation. Auxotrophic mutants of *P. methanolica* can be transformed with both homologous DNA (DNA from the host species) and heterologous DNA, and the resulting transformants can be used within a large number of diverse biological applications. The mutant cells of the present invention are particularly well suited for transformation with heterologous DNA, which transformed cells can be used for the production of polypeptides and proteins, including polypeptides and proteins of higher organisms, including humans. Auxotrophic *P. methanolica* cells can be transformed with other DNA molecules, including DNA libraries and synthetic DNA molecules. The invention thus provides host cells that can be used to express genetically diverse libraries to produce products that are screened for novel biological activities, can be engineered for use as targets for the screening of compound libraries, and can be genetically modified to enhance their utility within other processes.

Cells to be transformed with heterologous DNA will commonly have a mutation that can be complemented by a gene (a "selectable marker") on the heterologous DNA molecule. This selectable marker allows the transformed cells to grow under conditions in which untransformed cells cannot multiply ("selective conditions"). The general principles of selection are well known in the art. Commonly used selectable markers are genes that encode enzymes required for the synthesis of amino acids or nucleotides. Cells having mutations in these genes (auxotrophic mutants) cannot grow in media lacking the specific amino acid or nucleotide unless the mutation is complemented by the selectable marker. Use of such "selective" culture media ensures the stable maintenance of the heterologous DNA within the host cell. A preferred selectable marker of this type for use in *Pichia methanolica* is a *P. methanolica* ADE2 gene, which encodes phosphoribosyl-5-aminoimidazole carboxylase (AIRC; EC 4.1.1.21). The ADE2 gene, when transformed into an ade2 host cell, allows the cell to grow in the absence of adenine. The coding strand of a representative *P. methanolica* ADE2 gene sequence is shown in SEQ ID NO: 1. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments could be used as long as the coding portion is operably linked to promoter and terminator sequences. Those skilled in the art will recognize that this and other sequences provided herein represent single alleles of the respective genes, and that allelic variation is expected to exist. Any functional ADE2 allele can be used within the present invention. Other nutritional markers that can be used within the present invention include the *P. methanolica* ADE1, HIS3, and LEU2 genes, which allow for selection in the absence of adenine, histidine, and leucine, respectively. Heterologous genes, such as genes from other fungi, can also be used as selectable markers. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Gene-deficient mutants can be prepared by known methods, such as site-directed mutagenesis. *P. methanolica* genes can be cloned on the basis of homology with their counterpart *Saccharomyces cerevisiae* genes. The ADE2 gene disclosed herein was given its designation on the basis of such homology.

Strains of *Pichia methanolica* are available from the American Type Culture Collection (Rockville, Md.) and other repositories, and can be used as starting materials within the present invention. To prepare auxotrophic mutants of *P. methanolica*, cells are first exposed to mutagenizing conditions, i.e. environmental conditions that cause genetic mutations in the cells. Methods for mutagenizing cells are well known in the art and include chemical treatment, exposure to ultraviolet light, exposure to x-rays, and retroviral insertional mutagenesis. Chemical mutagens include ethylmethane sulfonate (EMS), N-methyl-N'-nitro-N-nitrosoguanidine, 2-methoxy-6-chloro-9-[3-(ethyl-2-chloroethyl)aminopropylamino]acridine2HCl, 5-bromouracil, acridine, and aflatoxin. See Lawrence, *Methods Enzymol.* 194:273–281, 1991. The proportion of mutagenized cells obtained is a function of the strength or amount of mutagenizing agent to which the cells are exposed. A low level of mutagen produces a small proportion of mutant cells. Higher levels of mutagen produce a higher proportion of mutant cells, but also kill more cells. It is therefore necessary to balance mutagenesis with killing so that a reasonable number of mutant cells is obtained. Balancing is generally done empirically by exposing cells to different conditions to establish a killing curve. In general, the cells are exposed to mutagenizing conditions and cultured for one day, after which they are tested for viability according to standard assay methods. Within the present invention, it is preferred to use a level of mutagenesis that results in 20–50% mortality, although one skilled in the art will recognize that this value can be adjusted as necessary, for example if working with a very large number of cells.

Mutagenized cells are then cultured in a rich medium to allow mutations to become established and replicated in at least a portion of the cell population. This step allows cells in which the genome has been altered to replicate the mutation and pass it on to their progeny, thereby establishing the mutation within the population.

The cells are then transferred to a culture medium deficient in assimilable nitrogen so that cellular nitrogen stores are depleted. By "deficient in assimilable nitrogen" it is meant that the medium lacks an amount of nitrogen sufficient to support growth of the cells. Depletion of cellular nitrogen stores will generally require about 12 to 24 hours of incubation, with 16 hours being sufficient under common conditions. Following depletion of nitrogen stores, the cells are cultured in a defined culture medium comprising an inorganic nitrogen source and an amount of an antifungal antibiotic sufficient to kill growing P. methanolica cells. A preferred antibiotic is nystatin (mycostatin). Preferred inorganic nitrogen sources are those comprising ammonium ions, such as ammonium sulfate. In general, the medium will contain 10–200 mM ammonium, preferably about 60 mM ammonium. Nystatin is included at a concentration of 0.1 to 100 mg/l, preferably 0.5 to 20 mg/L, more preferably about 2 mg/L (10 units/L). Treatment with nystatin is carried out for ten minutes to six hours, preferably about 1 hour. Those skilled in the art will recognize that the actual antibiotic concentration and exposure time required to kill protrophic cells can be readily determined empirically, and certain adjustments may be necessary to compensate for variations in specific activity between individual batches of antibiotic. By depleting cellular nitrogen stores and then culturing the cells in a defined medium containing an inorganic nitrogen source and antibiotic, cells that are auxotrophic for amino acid or nucleotide biosynthesis remain alive because they cannot grow in the defined medium. Growing cells are killed by the antibiotic. Following the antibiotic treatment, the cells are transferred to a rich culture medium.

Auxotrophic mutations are confirmed and characterized by determining the nutrient requirements of the treated cells. Replica plating is commonly used for this determination. Cells are plated on both rich medium and media lacking specific nutrients. Cells that do not grow on particularly plates are auxotrophic for the missing nutrient. Complementation analysis can be used for further characterization.

Heterologous DNA can be introduced into P. methanolica cells by any of several known methods, including lithium transformation (Hiep et al., Yeast 9:1189–1197, 1993; Tarutina and Tolstorukov, Abst. of the 15th International Specialized Symposium on Yeasts, Riga (USSR), 1991, 137; Ito et al., J. Bacteriol. 153:163, 1983; Bogdanova et al., Yeast 11:343, 1995), spheroplast transformation (Beggs, Nature 275:104, 1978; Hinnen et al., Proc. Natl. Acad. Sci. USA 75:1929, 1978; Cregg et al., Mol. Cell. Biol 5:3376, 1985), freeze-thaw polyethylene glycol transformation (Pichia Expression Kit Instruction Manual, Invitrogen Corp., San Diego, Calif., Cat. No. K1710-01), or electropotation, the latter method being preferred. Electropotation is the process of using a pulsed electric field to transiently permeabilize cell membranes, allowing macromolecules, such as DNA, to pass into cells. Electropotation has been described for use with mammalian (e.g., Neumann et al., EMBO J. 1:841–845, 1982) and fungal (e.g., Meilhoc et al., Bio/Technology 8:223–227, 1990) host cells. However, the actual mechanism by which DNA is transferred into the cells is not well understood. For transformation of P. methanolica, it has been found that electropotation is surprisingly efficient when the cells are exposed to an exponentially decaying, pulsed electric field having a field strength of from 2.5 to 4.5 kV/cm and a time constant ($\tau$) of from 1 to 40 milliseconds. The time constant $\tau$ is defined as the time required for the initial peak voltage $V_0$ to drop to a value of $V_0/e$. The time constant can be calculated as the product of the total resistance and capacitance of the pulse circuit, i.e., $\tau = R \times C$. Typically, resistance and capacitance are either preset or may be selected by the user, depending on the electropotation equipment selected. In any event, the equipment is configured in accordance with the manufacturer's instructions to provide field strength and decay parameters as disclosed above. Electropotation equipment is available from commercial suppliers (e.g., BioRad Laboratories, Hercules, Calif.).

DNA molecules for use in transforming P. methanolica will commonly be prepared as double-stranded, circular plasmids, which are preferably linearized prior to transformation. For polypeptide or protein production, the DNA molecules will include, in addition to the selectable marker disclosed above, an expression casette comprising a transcription promoter, a DNA segment (e.g., a cDNA) encoding the polypeptide or protein of interest, and a transcription terminator. These elements are operably linked to provide for transcription of the DNA segment of interest. It is preferred that the promoter and terminator be that of a P. methanolica gene. Useful promoters include those from constitutive and methanol-inducible promoters. Promoter sequences are generally contained within 1.5 kb upstream of the coding sequence of a gene, often within 1 kb or less. In general, regulated promoters are larger than constitutive promoters due the presence of regulatory elements. Methanol-inducible promoters, which include both positive and negative regulatory elements, may extend more than 1 kb upstream from the initiation ATG. Promoters are identified by function and can be cloned according to known methods.

A particularly preferred methanol-inducible promoter is that of a P. methanolica alcohol utilization gene. A representative coding strand sequence of one such gene, AUG1, is shown in SEQ ID NO:2. Within SEQ ID NO:2, the initiation ATG codon is at nucleotides 1355–1357. Nucleotides 1–23 of SEQ ID NO:2 are non-AUG1 polylinker sequence. It is particularly preferred to utilize as a promoter a segment comprising nucleotides 24–1354 of SEQ ID NO:2, although additional upstream sequence can be included. P. methanolica contains a second alcohol utilization gene, AUG2, the promoter of which can be used within the present invention. A partial DNA sequence of one AUG2 clone is shown in SEQ ID NO:9. AUG2 promoter segments used within the present invention will generally comprise nucleotides 91–169 of SEQ ID NO:9, although small truncations at the 3' end would not be expected to negate promoter function. Other useful promoters include those of the dihydroxyacetone synthase (DHAS), formate dehydrogenase (FMD), and catalase (CAT) genes. Genes encoding these enzymes from other species have been described, and their sequences are available (e.g., Janowicz et al., Nuc. Acids Res. 13:2043, 1985; Hollenberg and Janowicz, EPO publication 0 299 108; Didion and Roggenkamp, FEBS Lett. 303:113, 1992). Genes encoding these proteins can be cloned by using the known sequences as probes, or by aligning known sequences, designing primers based on the alignment, and amplifying P. methanolica DNA by the polymerase chain reaction (PCR).

Constitutive promoters are those that are not activated or inactivated by environmental conditions; they are always transcriptionally active. Preferred constitutive promoters for use within the present invention include those from glyceraldehyde-3-phosphate dehydrogenase, triose phosphate isomerase, and phosphoglycerate kinase genes of P. methanolica. These genes can be cloned by complementation in a host cell, such as a Saccharomyces cerevisiae cell, having a mutation in the counterpart gene. Mutants of this type are well known in the art. See, for example, Kawasaki and Fraenkel, *Biochem. Biophys. Res. Comm.* 108: 1107–1112, 1982; McKnight et al., *Cell* 46:143–147, 1986; Aguilera and Zimmermann, *Mol. Gen. Genet.* 202:83–89, 1986.

The DNA molecules will further include a selectable marker to allow for identification, selection, and maintenance of transformants. The DNA molecules may further contain additional elements, such an origin of replication and a selectable marker that allow amplification and maintenance of the DNA in an alternate host (e.g., *E. coli*). To facilitate integration of the DNA into the host chromosome, it is preferred to have the entire expression segment, comprising the promoter—gene of interest—terminator plus selectable marker, flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred such cleavage sites are those that are recognized by restriction endonucleases that cut infrequently within a DNA sequence, such as those that recognize 8-base target sequences (e.g., Not I).

Proteins that can be produced in *P. methanolica* include proteins of industrial and pharmaceutical interest. Such proteins include higher eukaryotic proteins from plants and animals, particularly vertebrate animals such as mammals, although certain proteins from microorganisms are also of great value. Proteins that can be prepared using methods of the present invention include enzymes such as lipases, cellulases, and proteases; enzyme inhibitors, including protease inhibitors; growth factors such as platelet derived growth factor, fibroblast growth factors, and epidermal growth factor; cytokines such as erythropoietin and thrombopoietin; and hormones such as insulin, leptin, and glucagon.

For production of polypeptides, *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium is YEPD (Table 1). The cells may be passaged by dilution into fresh culture medium or stored for short periods on plates under refrigeration. For long-term storage, the cells are preferably kept in a 50% glycerol solution at −70° C.

Table 1

YEPD
  2% D-glucose
  2% Bacto™ Peptone (Difco Laboratories, Detroit, Mich.)
  1% Bacto™ yeast extract (Difco Laboratories)
  0.004% adenine
  0.006% L-leucine ADE D
  0.056% -Ade-Trp-Thr powder
  0.67% yeast nitrogen base without amino acids
  2% D-glucose
  0.5% 200X tryptophan, threonine solution ADE DS
  0.056% -Ade-Trp-Thr powder
  0.67% yeast nitrogen base without amino acids
  2% D-glucose
  0.5% 200X tryptophan, threonine solution
  18.22% D-sorbitol LEU D
  0.052% -Leu-Trp-Thr powder
  0.67% yeast nitrogen base without amino acids
  2% D-glucose
  0.5% 200X tryptophan, threonine solution HIS D
  0.052% -His-Trp-Thr powder
  0.67% yeast nitrogen base without amino acids
  2% D-glucose
  0.5% 200X tryptophan, threonine solution URA D
  0.056% -Ura-Trp-Thr powder
  0.67% yeast nitrogen base without amino acids
  2% D-glucose
  0.5% 200X tryptophan, threonine solution URA DS
  0.056% -Ura-Trp-Thr powder
  0.67% yeast nitrogen base without amino acids
  2% D-glucose
  0.5% 200X tryptophan, threonine solution
  18.22% D-sorbitol -Leu-Trp-Thr powder
  powder made by combining 4.0 g adenine, 3.0 g arginine, 5.0 g aspartic acid, 2.0 g histidine, 6.0 g isoleucine, 4.0 g lysine, 2.0 g methionine, 6.0 g phenylalanine, 5.0 g serine, 5.0 g tyrosine, 4.0 g uracil, and 6.0 g valine (all L-amino acids)

-His-Trp-Thr powder
  powder made by combining 4.0 g adenine, 3.0 g arginine, 5.0 g aspartic acid, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)

-Ura-Trp-Thr powder
  powder made by combining 4.0 g adenine, 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, and 6.0 g valine (all L-amino acids)

-Ade-Trp-Thr powder
  powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)

200X tryptophan, threonine solution
  3.0% L-threonine, 0.8% L-tryptophan in $H_2O$ For plates, add 1.8% Bacto™ agar (Difco Laboratories)

Electroporation of *P. methanolica* is preferably carried out on cells in early log phase growth. Cells are streaked to single colonies on solid media, preferably solid YEPD. After about 2 days of growth at 30° C., single colonies from a fresh plate are used to inoculate the desired volume of rich culture media (e.g., YEPD) to a cell density of about $5$–$10 \times 10^5$ cells/ml. Cells are incubated at about 25°–35° C., preferably 30° C., with vigorous shaking, until they are in early log phase. The cells are then harvested, such as by centrifugation at 3000×g for 2–3 minutes, and resuspended. Cells are made electrocompetent by reducing disulfide bonds in the cell walls, equilibrating them in an ionic solution that is compatible with the electroporation conditions, and chilling them. Cells are typically made electrocompetent by incubating them in a buffered solution at pH 6–8 containing a reducing agent, such as dithiothreitol (DTT) or β-mercaptoethanol (BME), to reduce cell wall proteins to facilitate subsequent uptake of DNA. A preferred incubation buffer in this regard is a fresh solution of 50 mM potassium phosphate buffer, pH 7.5, containing 25 mM DTT. The cells are incubated in this buffer (typically using one-fifth the original culture volume) at about 30° C. for about 5 to 30 minutes, preferably about 15 minutes. The cells are then harvested and washed in a suitable electroporation buffer, which is used ice-cold. Suitable buffers in this regard include pH 6–8 solutions containing a weak buffer, divalent cations (e.g., $Mg^{++}$, $Ca^{++}$) and an osmotic stabilizer (e.g., a sugar). After washing, the cells are resuspended in a small volume of the buffer, at which time they are electrocompetent and can be used directly or aliquotted and stored frozen (preferably at −70° C.). A preferred electroporation buffer is STM (270 mM sucrose, 10 mM Tris, pH 7.5, 1 mM $MgCl_2$). Within a preferred protocol, the cells are subjected to two washes, first in the original culture volume of ice-cold buffer, then in one-half the original volume. Following the second wash, the cells are harvested and resuspended, typically using about 3–5 ml of buffer for an original culture volume of 200 ml.

Electroporation is carried out using a small volume of electrocompetent cells (typically about 100 µl) and up to one-tenth volume of linear DNA molecules. For example, 0.1 ml of cell suspension in a buffer not exceeding 50 mM in ionic strength is combined with 0.1–10 µg of DNA (vol.≦10 µl). This mixture is placed in an ice-cold electroporation cuvette and subjected to a pulsed electric field of from 2.5 to 4.5 kV/cm, preferably about 3.75 kV/cm, and a time constant of from 1 to 40 milliseconds, preferably 10–30 milliseconds, more preferably 15–25 milliseconds, most preferably about 20 milliseconds, with exponential decay. The actual equipment settings used to achieve the desired pulse parameters will be determined by the equipment used. When using a BioRad (Hercules, Calif.) Gene Pulser™ electroporator with a 2 mm electroporation cuvette, resistance is set at 600 ohms or greater, preferably "infinite" resistance, and capacitance is set at 25 µF to obtain the desired field characteristics. After being pulsed, the cells are diluted approximately 10X into 1 ml of YEPD broth and incubated at 30° C. for one hour.

The cells are then harvested and plated on selective media. Within a preferred embodiment, the cells are washed once with a small volume (equal to the diluted volume of the electroporated cells) of 1X yeast nitrogen base (6.7 g/L yeast nitrogen base without amino acids; Difco Laboratories, Detroit, Mich.), and plated on minimal selective media. Cells having an ade2 mutation that have been transformed with an ADE2 selectable marker can be plated on a minimal medium that lacks adenine, such as ADE D (Table 1) or ADE DS (Table 1). In a typical procedure, 250 µl aliqouts of cells are plated on 4 separate ADE D or ADE DS plates to select for $Ade^+$ cells.

*P. methanolica* recognizes certain infrequently occuring sequences, termed autonomously replicating sequences (ARS), as origins of DNA replication, and these sequences may fortuitously occur within a DNA molecule used for transformation, allowing the transforming DNA to be maintained extrachromosomally. However, integrative transformants are generally preferred for use in protein production systems. Integrative transformants have a profound growth advantage over ARS transformants on selective media containing sorbitol as a carbon source, thereby providing a method for selecting integrative transformants from among a population of transformed cells. ARS sequences have been found to exist in the ADE2 gene and, possibly, the AUG1 gene of *P. methanolica*. ade2 host cells of *Pichia methanolica* transformed with an ADE2 gene can thus become $Ade^+$ by at least two different modes. The ARS within the ADE2 gene allows unstable extrachromosomal maintenance of the transforming DNA (Hiep et al., *Yeast* 9:1189–1197, 1993). Colonies of such transformants are characterized by slower growth rates and pink color due to prolific generation of progeny that are $Ade^-$. Transforming DNA can also integrate into the host genome, giving rise to stable transformants that grow rapidly, are white, and that fail to give rise to detectable numbers of $Ade^-$ progeny. ADE D plates allow the most rapid growth of transformed cells, and unstable and stable transformants grow at roughly the same rates. After 3–5 days of incubation on ADE D plates at 30° C. stable transformant colonies are white and roughly twice the size of unstable, pink transformants. ADE DS plates are more selective for stable transformants, which form large (≈5 mm) colonies in 5–7 days, while unstable (ARS-maintained) colonies are much smaller (≈1 mm). The more selective ADE DS media is therefore preferred for the identification and selection of stable transformants. For some applications, such as the screening of genetically diverse libraries for rare combinations of genetic elements, it is sometimes desirable to screen large numbers of unstable transformants, which have been observed to outnumber stable transformants by a factor of roughly 100. In such cases, those skilled in the art will recognize the utility of plating transformant cells on less selective media, such as ADE D.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette and differences in promoter activity among individual isolates. It is therefore advantageous to screen a number of isolates for expression level prior to selecting a production strain. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 µg/L biotin, and 0.56 g/L of -Ade-Thr-Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 mL of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 µg/L biotin) at a cell density of about $1\times10^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1-2 days with vigorous agititation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter. The use of glucose in combination with methanol under glucose-limited conditions produces rapid growth, efficient conversion of carbon to biomass and rapid changes in physiological growth states, while still providing full induction of methanol-inducible gene promoters. In a typical fermentation run, a cell density of from about 80 to about 400 grams of wet cell paste per liter is obtained. "Wet cell paste" refers to the mass of cells obtained by harvesting the cells from the fermentor, typically by centrifugation of the culture.

The invention is further illustrated by the following non-limiting examples.

EXAMPLES

Example 1

*P. methanolica* cells (strain CBS6515 from American Type Culture Collection, Rockville, Md.) were mutagenized by UV exposure. A killing curve was first generated by plating cells onto several plates at approximately 200-250 cells/plate. The plates were then exposed to UV radiation using a GST5 germicidal lamp (Sylvania) suspended 25 cm from the surfaces of the plates for periods of time as shown in Table 2. The plates were then protected from visible light sources and incubated at 30° C. for two days.

TABLE 2

| | Viable Cells | | |
|---|---|---|---|
| Time | Plate 1 | Plate 2 | Average |
| 0 sec. | 225 | 229 | 227 |
| 1 sec. | 200 | 247 | 223 |
| 2 sec. | 176 | 185 | 181 |
| 4 sec. | 149 | 86 | 118 |
| 8 sec. | 20 | 7 | 14 |
| 16 sec. | 0 | 2 | 1 |

Large-scale mutagenesis was then carded out using a 2-second UV exposure to provide about 20% killing. Cells were plated at approximately $10^4$ cells/plate onto eight YEPD plates that were supplemented with 100 mg/L each of uracil, adenine, and leucine, which were added to supplement the growth of potential auxotrophs having the cognate deficiencies. Following UV exposure the plates were wrapped in foil and incubated overnight at 30° C. The following day the colonies on the plates ($\sim 10^5$ total) were resuspended in water and washed once with water. An amount of cell suspension sufficient to give an $OD_{600}$ of 0.1–0.2 was used to inoculate 500 ml of minimal broth made with yeast nitrogen base without amino acids or ammonia, supplemented with 1% glucose and 400 µg/L biotin. The culture was placed in a 2.8 L baffled Bell flask and shaken vigorously overnight at 30° C. The following day the cells had reached an $OD_{600}$ of ~1.0–2.0. The cells were pelleted and resuspended in 500 ml of minimal broth supplemented with 5 g/L ammonium sulfate. The cell suspension was placed in a 2.8 L baffled Bell flask and shaken vigorously at 30° C. for 6 hours. 50 ml of the culture was set aside in a 250-ml flask as a control, and to the remainder of the culture was added 1 mg nystatin (Sigma Chemical Co., St. Louis, Mo.) to select for auxotrophic mutants (Snow, *Nature* 211:206–207, 1966). The cultures were incubated with shaking for an additional hour. The control and nystatin-treated cells were then harvested by centrifugation and washed with water three times. The washed cells were resuspended to an $OD_{600}$ of 1.0 in 50% glycerol and frozen. Titering of nystatin-treated cells versus the control cells for colony forming traits revealed that nystatin enrichment had decreased the number of viable cells by a factor of $10^4$.

$10^{-2}$ dilutions of nystatin-treated cells were plated on 15 YEPD plates. Colonies were replica-plated onto minimal plates (2% agar, 1×YNB, 2% glucose, 400 µg/L biotin). The frequency of auxotrophs was about 2–4%. Approximately 180 auxotrophic colonies were picked to YEPD+Ade, Leu, Ura plates and replica-plated to various dropout plates. All of the auxotrophs were Ade⁻. Of these, 30 were noticably pink on dropout plates (LEU D, HIS D, etc.; see Table 1). Of the 30 pink mutants, 21 were chosen for further study; the remainder were either leaky for growth on ADE D plates or contaminated with wild-type cells.

The Ade⁻ mutants were then subjected to complementation analysis and phenotypic testing. To determine the number of loci defined by the mutants, all 21 mutants were mated to a single pink, Ade⁻ tester strain (strain #2). Mating was carried out by mixing cell suspensions ($OD_{600}$=1) and plating the mixtures in 10 µl aliquots on YEPD plates. The cells were then replicated to SPOR media (0.5% Na acetate, 1% KCl, 1% glucose, 1% agar) and incubated overnight at 30° C. The cells were then replica-plated to ADE D plates for scoring of phenotype. As shown in Table 3, some combinations of mutants failed to give Ade⁺ colonies (possibly defining the same genetic locus as in strain #2), while others gave rise to numerous Ade$^+$ colonies (possibly defining a separate genetic locus). Because mutant #3 gave Ade$^+$ colonies when mated to #2, complementation testing was repeated with mutant #3. If the group of mutants defined two genetic loci, then all mutants that failed to give Ade$^+$ colonies when mated to strain #2 should give Ade$^+$ colonies when mated to #3. Results of the crosses are shown in Table 3.

TABLE 3

| Mutant | × Mutant #2 | × Mutant #3 |
|---|---|---|
| #1 | + | − |
| #3 | + | − |
| #10 | + | − |
| #15 | + | − |
| #18 | + | − |
| #24 | + | − |
| #28 | + | − |
| #30 | + | − |
| #2 | − | + |
| #6 | − | + |
| #8 | − | + |
| #9 | − | + |
| #11 | − | + |
| #17 | − | + |
| #19 | − | + |
| #20 | − | + |
| #22 | − | + |
| #27 | + | + |
| #4 | + | + |
| #12 | + | + |
| #16 | + | + |

As shown in Table 3, most mutants fell into one of two groups, consistent with the idea that there are two adenine biosynthetic genes that, when missing, result in pink colonies on limiting adenine media. Three colonies (#4, #12, and #16) may either define a third locus or exhibit intragenic complementation. Two intensely pigmented mutants from each of the two complementation groups (#3 and #10; #6 and #11) were selected for further characterization. Additional analysis indicated that Ade$^−$ was the only auxotrophy present in these strains.

A P. methanolica clone bank was constructed in the vector pRS426, a shuttle vector comprising 2µ and S. cerevisiae URA3 sequences, allowing it to be propagated in S. cerevisiae. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated in E. coli MC1061 cells using a BioRad Gene Pulser™ device as recommended by the manufacturer.

The genomic library was used to transform S. cerevisiae strain HBY21A (ade2 ura3) by electroporation (Becker and Guarente, Methods Enzymol. 194:182–187, 1991). The cells were resuspended in 1.2M sorbitol, and six 300-µl aliquots were plated onto ADE D, ADE DS, URA D and URA DS plates (Table 1). Plates were incubated at 30° C. for 4–5 days. No Ade$^+$ colonies were recovered on the ADE D or ADE DS plates. Colonies from the URA D and URA DS plates were replica-plated to ADE D plates, and two closely spaced, white colonies were obtained. These colonies were restreaked and confirmed to be Ura$^+$ and Ade$^+$. These two strains, designated Ade1 and Ade6, were streaked onto media containing 5 FOA (5 fluoro orotic acid; Sikorski and Boeke, Methods Enzymol. 194:302–318). Ura$^−$ colonies were obtained, which were found to be Ade$^−$ upon replica plating. These results indicate that the Ade$^+$ complementing activity is genetically linked to the plasmid-borne URA3 marker. Plasmids obtained from yeast strains Ade1 and Ade6 appeared to be identical by restriction mapping as described below. These genomic clones were designated pADE1-1 and pADE1-6, respectively.

Total DNA was isolated from the HBY21A transformants Ade1 and Ade6 and used to transform E. coli strain MC1061 to Amp$^R$. DNA was prepared from 2 Amp$^R$ colonies of Ade1 and 3 Amp$^R$ colonies of Ade6. The DNA was digested with Pst I, Sca I, and Pst I+Sca I and analyzed by gel electrophoresis. All five isolates produced the same restriction pattern.

PCR primers were designed from the published sequence of the P. methanolica ADE2 gene (also known as ADE1; Hiep et al., Yeast 9:1251–1258, 1993). Primer 9080 (SEQ ID NO:3) was designed to prime at bases 406–429 of the ADE2 DNA (SEQ ID NO:1), and primer 9079 (SEQ ID NO:4) was designed to prime at bases 2852–2829. Both primers included tails to introduce Avr II and Spe I sites at each end of the amplified sequence. The predicted size of the resulting PCR fragment was 2450 bp.

PCR was carried out using plasmid DNA from the five putative ADE2 clones as template DNA. The 100 µl reaction mixtures contained 1×Taq PCR buffer (Boehringer Mannheim, Indianapolis, Ind.), 10–100 ng of plasmid DNA, 0.25 mM dNTPs, 100 pmol of each primer, and 1 µl Taq polymerase (Boehringer Mannheim). PCR was run for 30 cycles of 30 seconds at 94° C., 60 seconds at 50° C., and 120 seconds at 72° C. Each of the five putative ADE2 genomic clones yielded a PCR product of the expected size (2.4 kb). Restriction mapping of the DNA fragment from one reaction gave the expected size fragments when digested with Bgl II or Sal I.

The positive PCR reactions were pooled and digested with Spe I. Vector pRS426 was digested with Spe I and treated with calf intestinal phosphatase. Four µl of PCR fragment and 1 µl of vector DNA were combined in a 10 µl reaction mix using conventional ligation conditions. The ligated DNA was analyzed by gel electrophoresis. Spe I digests were analyzed to identify plasmids carrying a subclone of the ADE2 gene within pRS426. The correct plasmid was designated pCZR118.

Because the ADE2 gene in pCZR118 had been amplified by PCR, it was possible that mutations that disabled the functional character of the gene could have been generated. To test for such mutations, subclones with the desired insert were transformed singly into Saccharomyces cerevisiae strain HBY21A. Cells were made electrocompetent and transformed according to standard procedures. Transformants were plated on URA D and ADE D plates. Three phenotypic groups were identified. Clones 1, 2, 11, and 12 gave robust growth of many transformants on ADE D. The transformation frequency was comparable to the frequency of Ura$^+$ transformants. Clones 6, 8, 10, and 14 also gave a high efficiency of transformation to both Ura+ and Ade+, but the Ade+ colonies were somewhat smaller than those in the first group. Clone 3 gave many Ura+ colonies, but no Ade+ colonies, suggesting it carried a non-functional ade2 mutation. Clones 1, 2, 11, and 12 were pooled.

To identify the *P. methanolica* ade2 complementation group, two representative mutants from each complementation group (#3 and #10; #6 and #11), which were selected on the basis of deep red pigmentation when grown on limiting adenine, were transformed with the cloned ADE gene. Two hundred ml cultures of early log phase cells were harvested by centrifugation at 3000×g for 3 minutes and resuspended in 20 ml of fresh KD buffer (50 mM potassium phosphate buffer, pH 7.5, containing 25 mM DTT). The cells were incubated in this buffer at 30° C. for 15 minutes. The cells were then harvested and resuspended in 200 ml of ice-cold STM (270 mM sucrose, 10 mM Tris, pH 7.5, 1 mM MgCl$_2$). The cells were harvested and resuspended in 100 ml of ice-cold STM. The cells were again harvested and resuspended in 3–5 ml of ice-cold STM. 100-µl aliquouts of electrocompetent cells from each culture were then mixed with Not I-digested pADE1-1 DNA. The cell/DNA mixture was placed in a 2 mm electroporation cuvette and subjected to a pulsed electric field of 5 kV/cm using a BioRad Gene Pulser™ set to 1000 Ω resistance and capacitance of 25 µF. After being pulsed, the cells were diluted by addition of 1 ml YEPD and incubated at 30° C. for one hour. The cells were then harvested by gentle centrifugation and resuspended in 400 µl minimal selective media lacking adenine (ADE D). The resuspended samples were split into 200-µl aliqouts and plated onto ADE D and ADE DS plates. Plates were incubated at 30° C. for 4–5 days. Mutants #6 and #11 gave Ade+ transformants. No Ade+ transformants were observed when DNA was omitted, hence the two isolates appeared to define the ade2 complementation group. The ADE2 sequence is shown in SEQ ID NO:1.

Example 2

The *P. methanolica* clone bank disclosed in Example 1 was used as a source for cloning the Alcohol Utilization Gene (AUG1). The clone bank was stored as independent pools, each representing about 200–250 individual genomic clones. 0.1 µl of "miniprep" DNA from each pool was used as a template in a polymerase chain reaction with PCR primers (8784, SEQ ID NO:5; 8787, SEQ ID NO:6) that were designed from an alignment of conserved sequences in alcohol oxidase genes from *Hansenula polymorpha*, *Candida boidini*, and *Pichia pastoris*. The amplification reaction was run for 30 cycles of 94° C., 30 seconds; 50° C., 30 seconds; 72° C., 60 seconds; followed by a 7 minute incubation at 72° C. One pool (#5) gave a ~600 bp band. DNA sequencing of this PCR product revealed that it encoded an amino acid sequence with ~70% sequence identity with the *Pichia pastoris* alcohol oxidase encoded by the AOX1 gene and about 85% sequence identity with the *Hansenula polymorpha* alcohol oxidase encoded by the MOX1 gene. The sequence of the cloned AUG1 gene is shown in SEQ ID NO:2.

Sub-pools of pool #5 were analyzed by PCR using the same primers used in the initial amplification. One positive sub-pool was further broken down to identify a positive colony. This positive colony was streaked on plates, and DNA was prepared from individual colonies. Three colonies gave identical patterns after digestion with Cla I.

Restriction mapping of the genomic clone and PCR product revealed that the AUG1 gene lay on a 7.5 kb genomic insert and that sites within the PCR fragment could be uniquely identified within the genomic insert. Because the orientation of the gene within the PCR fragment was known, the latter information provided the approximate location and direction of transcription of the AUG1 gene within the genomic insert. DNA sequencing within this region revealed a gene with very high sequence similarity at the amino acid level to other known alcohol oxidase genes.

Example 3 ade2 mutant *P. methanolica* cells are transformed by electroporation essentially as disclosed above with an expression vector comprising the AUG1 promoter and terminator, human GAD65 DNA (Karlsen et al., *Proc. Natl. Acad. Sci. USA* 88:8337–8341, 1991), and ADE2 selectable marker. Colonies are patched to agar minimal methanol plates (10 to 100 colonies per 100-mm plate) containing 20 g/L Bacto™-agar (Difco), 6.7 g/L yeast nitrogen base without amino acids (Difco), 10 g/L methanol, and 0.4 µg/L biotin. The agar is overlayed with nitrocellulose, and the plates are inverted over lids containing 1 ml of 50% methanol in water and incubated for 3 to 5 days at 30° C. The membrane is then transferred to a filter soaked in 0.2M NaOH, 0.1% SDS, 35 mM dithiothreitol to lyse the adhered cells. After 30 minutes, cell debris is rinsed from the filter with distilled water, and the filter is neutralized by rinsing it for 30 minutes in 0.1M acetic acid.

The filters are then assayed for adhered protein. Unoccupied binding sites are blocked by rinsing in TTBS-NFM (20 mM Tris pH 7.4, 0.1% Tween 20, 160 mM NaCl, 5% powdered nonfat milk) for 30 minutes at room temperature. The filters are then transferred to a solution containing GAD6 monoclonal antibody (Chang and Gottlieb, *J. Neurosci.* 8:2123–2130, 1988), diluted 1:1000 in TTBS-NFM. The filters are incubated in the antibody solution with gentle agitation for at least one hour, then washed with TTBS (20 mM Tris pH 7.4, 0.1% Tween 20, 160 mM NaCl) two times for five minutes each. The filters are then incubated in goat anti-mouse antibody conjugated to horseradish peroxidase (1 µg/ml in TTBS-NFM) for at least one hour, then washed three times, 5 minutes per wash with TTBS. The filters are then exposed to commercially available chemiluminescence reagents (ECL™; Amersham Inc., Arlington Heights, Ill.). Light generated from positive patches is detected on X-ray film.

To more accurately detect the level of $GAD_{65}$ expression, candidate clones are cultured in shake flask cultures. Colonies are grown for two days on minimal methanol plates at 30° C. as disclosed above. The colonies are used to inoculate 20 ml of minimal methanol media (6.7 g/L yeast nitrogen base without amino acids, 10 g/L methanol, 0.4 µg/L biotin) at a cell density of $1\times10^6$ cells/ml. The cultures are grown for 1–2 days at 30° C. with vigorous shaking. 0.2 ml of 50% methanol is added to each culture daily. Cells are harvested by centrifugation and suspended in ice-cold lysis buffer (20 mM Tris pH 8.0, 40 mM NaCl, 2 mM PMSF, 1 mM EDTA, 1 µg/ml leupeptin, 1 µg/ml pepstatin, 1 µg/ml aprotinin) at 10 ml final volume per 1 g cell paste. 2.5 ml of the resulting suspension is added to 2.5 ml of 400–600 micron, ice-cold, acid-washed glass beads in a 15-ml vessel, and the mixture is vigorously agitated for one minute, then incubated on ice for 1 minute. The procedure is repeated until the cells have been agitated for a total of five minutes. Large debris and unbroken cells are removed by centrifugation at 1000×g for 5 minutes. The clarified lysate is then decanted to a clean container. The cleared lysate is diluted in sample buffer (5% SDS, 8M urea, 100 mM Tris pH 6.8, 10% glycerol, 2 mM EDTA, 0.01% bromphenol glue) and electrophoresed on a 4–20% acrylamide gradient gel (Novex, San Diego, Calif.). Proteins are blotted to nitrocellose and detected with GAD6 antibody as disclosed above.

Clones exhibiting the highest levels of methanol-induced expression of foreign protein in shake flask culture are more extensively analyzed under high cell density fermentation conditions. Cells are first cultivated in 0.5 liter of YEPD broth at 30° C. for 1–2 days with vigorous agitation, then used to inoculate a 5-liter fermentation apparatus (e.g., BioFlow III; New Brunswick Scientific Co., Inc., Edison, N.J.). The fermentation vessel is first charged with mineral salts by the addition of 57.8 g $(NH_4)_2SO_4$, 68 g $KH_2PO_4$, 30.8 g $MgSO_4.7H_2O$, 8.6 g $CaSO_4.2H_2O$, 2.0 g NaCl, and 10 ml antifoam (PPG). $H_2O$ is added to bring the volume to 2.5 L, and the solution is autoclaved 40 minutes. After cooling, 350 ml of 50% glucose, 250 ml 10 X trace elements (Table 4), 25 ml of 200 µg/ml biotin, and 250 ml cell inoculum are added.

TABLE 4

| 10 × trace elements: | | |
|---|---|---|
| $FeSO_4.7H_2O$ | 100 mM | 27.8 g/L |
| $CuSO_4.5H_2O$ | 2 mM | 0.5 g/L |
| $ZnCl_2$ | 8 mM | 1.09 g/L |
| $MnSO_4.H_2O$ | 8 mM | 1.35 g/L |
| $CoCl_2.6H_2O$ | 2 mM | 0.48 g/L |
| $Na_2MoO_4.2H_2O$ | 1 mM | 0.24 g/L |
| $H_3BO_3$ | 8 mM | 0.5 g/L |
| KI | 0.5 mm | 0.08 g/L |
| biotin | | 5 mg/L |
| thiamine | | 0.5 g/L |

Add 1–2 mls $H_2SO_4$ per liter to bring compounds into solution.

The fermentation vessel is set to run at 28° C., pH 5.0, and >30% dissolved $O_2$. The cells will consume the initial charge of glucose, as indicated by a sharp demand for oxygen during glucose consumption followed by a decrease in oxygen consumption after glucose is exhausted. After exhaustion of the initial glucose charge, a glucose-methanol feed supplemented with $NH_4^+$ and trace elements is delivered into the vessel at 0.2% (w/v) glucose, 0.2% (w/v) methanol for 5 hours followed by 0.1% (w/v) glucose, 0.4% (w/v) methanol for 25 hours. A total of 550 grams of methanol is supplied through one port of the vessel as pure methanol using an initial delivery rate of 12.5 ml/hr and a final rate of 25 ml/hr. Glucose is supplied through a second port using a 700 ml solution containing 175 grams glucose, 250 ml 10X trace elements, and 99 g $(NH_4)_2SO_4$. Under these conditions the glucose and methanol are simultaneously utilized, with the induction of $GAD_{65}$ expression upon commencement of the glucose-methanol feed. Cells from the fermentation vessel are analyzed for $GAD_{65}$ expression as described above for shake flask cultures.

Cells are removed from the fermentation vessel at certain time intervals and subsequently analyzed. Little $GAD_{65}$ expression is observed during growth on glucose. Exhaustion of glucose leads to low level expression of the $GAD_{65}$ protein; expression is enhanced by the addition of MeOH during feeding of the fermentation culture. The addition of methanol has a clear stimulatory effect of the expresion of human $GAD_{65}$ driven by the methanol-responsive AUG1promoter.

Example 4

Transformation conditions were investigated to determine the electric field conditions, DNA topology, and DNA concentration that were optimal for efficient transformation of *P. methanolica*. All experiments used *P. methanolica* ade2 strain #11. Competent cells were prepared as previously described. Electroporation was carried out using a BioRad Gene Pulser™.

Three field parameters influence transformation efficiency by electroporation: capacitance, field strength, and pulse duration. Field strength is determined by the voltage of the electric pulse, while the pulse duration is determined by the resistance setting of the instrument. Within this set of experiments, a matrix of field strength settings at various resistances was examined. In all experiments, the highest capacitance setting (25 µF) of the instrument was used. 100 µl aliquots of electrocompetent cells were mixed on ice with 10 µl of DNA that contained approximately 1 µg of the ADE2 plasmid pCZR133 that had been linearized with the restriction enzyme Not I. Cells and DNA were transferred to 2 mm electroporation cuvettes (BTX Corp., San Diego, Calif.) and electropulsed at field strengths of 0.5 kV (2.5 kV/cm), 0.75 kV (3.75 kV/cm), 1.0 kV (5.0 kV/cm), 1.25 kV (6.25 kV/cm), and 1.5 kV (7.5 kV/cm). These field strength conditions were examined at various pulse durations. Pulse duration was manipulated by varying the instrument setting resistances to 200 ohms, 600 ohms, or "infinite" ohms. Pulsed cells were suspended in YEPD and incubated at 30° C. for one hour, harvested, resuspended, and plated. Three separate sets of experiments were conducted. In each set, electropotation conditions of 0.75 kV (3.75 kV/cm) at a resistance of "infinite" ohms was found to give a dramatically higher transformation efficiency than other conditions tested (see FIG. 1).

After the optimal pulse conditions were established, the influence of DNA topology on transformation efficiency was investigated. Electrocompetent cells were mixed with 1 µg of uncut, circular pCZR133 or with 1 µg of Not I-digested pCZR133. In three separate experiments, an average of roughly 25 transformants were recovered with circular DNA while linear DNA yielded an average of nearly $1 \times 10^4$ transformants. These data indicate that linear DNA transforms *P. methanolica* with much greater efficiency than circular DNA.

Finally, the relationship between DNA concentration and transformation efficiency was investigated. Aliquots of linear pCZR133 DNA (1 ng, 10 ng, 100 ng and 1 µg in 10 µl $H_2O$) were mixed with 100 µl electrocompetent cells, and electropotation was carried out at 3.75 kV/cm and "infinite" ohms. The number of transformants varied from about 10 (1 ng DNA) to $10^4$ (1 µg DNA) and was found to be proportional to the DNA concentration.

Example 5

Integration of transforming DNA into the genome of *P. methanolica* was detected by comparison of DNA from wild-type cells and stable, white transformant colonies. Two classes of integrative transformants were identified. In the first, transforming DNA was found to have integrated into a homologous site. In the second class, transforming DNA was found to have replaced the endogenous AUG1 open reading frame. While not wishing to be bound by theory, this second transformant is believed to have arisen by a "transplacement recombination event" (Rothstein, *Methods Enzymol.* 194:281–301, 1991) whereby the transforming DNA replaces the endogenous DNA via a double recombination event.

Figure 2:
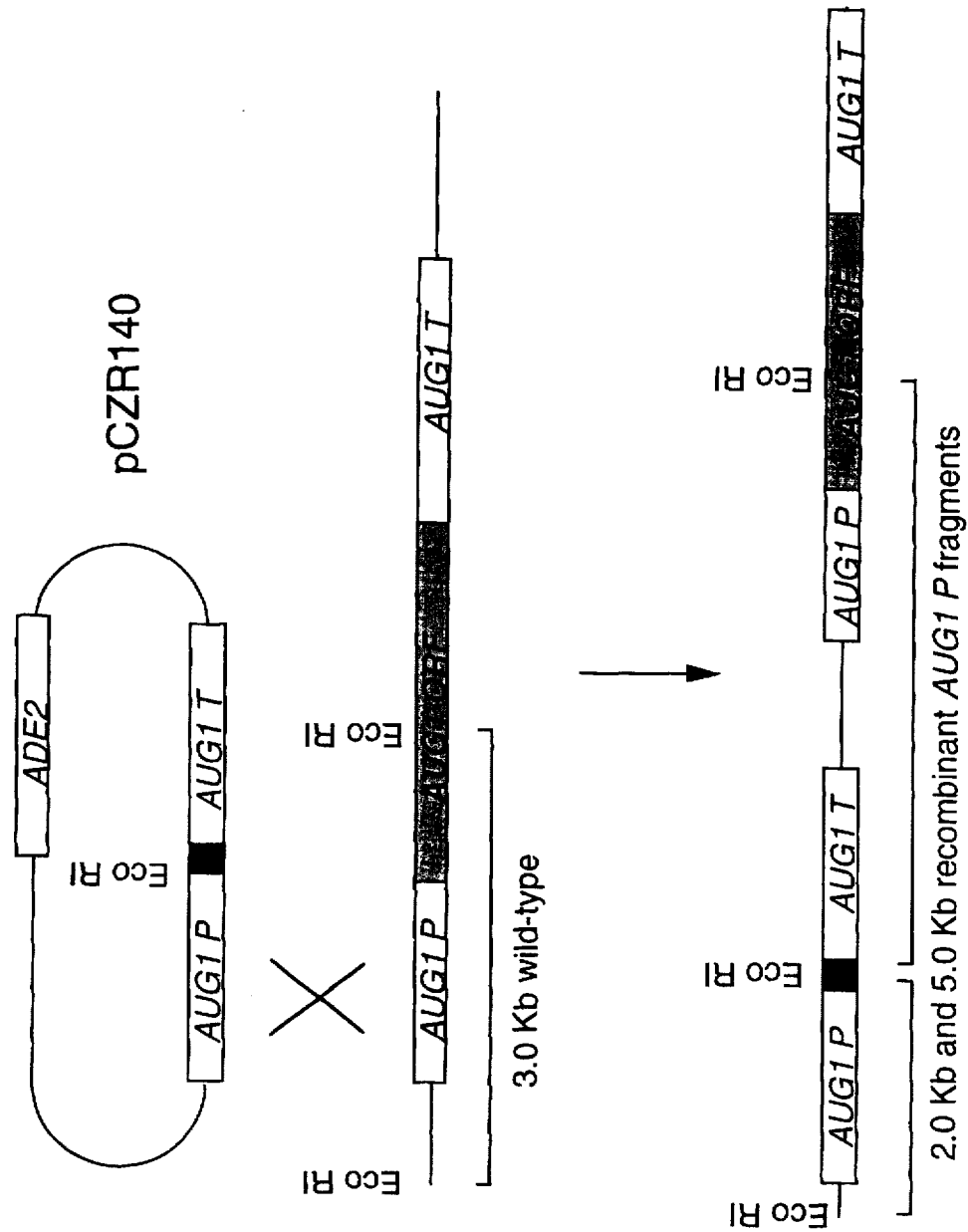
FIG. 2 is a schematic diagram of a recombination event between plasmid pCZR140 and *P. methanolica* genomic DNA.

*P. methanolica* ade2 strain #11 was transformed to Ade⁺ with Asp I-digested pCZR140, a Bluescript® (Stratagene Cloning Systems, La Jolla, Calif.)-based vector containing the *P. methanolica* ADE2 gene and a mutant of AUG1 in which the entire open reading frame between the promoter and terminator regions has been deleted (FIG. 2). Genomic DNA was prepared from wild-type and transformant cells grown for two days on YEPD plates at 30° C. About 100–200 μl of cells was suspended in 1 ml H$_2$O, then centrifuged in a microcentrifuge for 30 seconds. The cell pellet was recovered and resuspended in 400 μl of SCE+ DTT+zymolyase (1.2M sorbitol, 10 mM Na titrate, 10 mM EDTA, 10 mM DTT, 1–2 mg/ml zymolyase 100T) and incubated at 37° C. for 10–15 minutes. 400 μl of 1% SDS was added, and the solution was mixed until clear. 300 μl of 5M potassium acetate, pH 8.9 was added, and the solution was mixed and centrifuged at top speed in a microcentrifuge for five minutes. 750 μl of the supernatant was transferred to a new tube and extracted with an equal volume of phenol/chloroform. 600 μl of the resulting supernatant was recovered, and DNA was precipitated by the addition of 2 volumes of ethanol and centrifugation for 15 minutes in the cold. The DNA pellet was resuspended in 50 ml TE (10 mM Tris pH 8, 1 mM EDTA)+100 μg/ml RNAase for about 1 hour at 65° C. 10-μl DNA samples were digested with Eco RI (5 μl) in a 100 μl reaction volume at 37° C. overnight. DNA was precipitated with ethanol, recovered by centrifugation, and resuspended in 7.5 μl TE+2.5 μl 5X loading dye. The entire 10 ml volume was applied to one lane of a 0.7% agarose in 0.5 X TBE (10 X TBE is 108 g/L Tris base 7–9, 55 g/L boric acid, 8.3 g/L disodium EDTA) gel. The get was run at 100 V in 0.5 X TBE containing ethidium bromide. The gel was photographed, and DNA was electrophoretically transferred to a positively derivatized nylon membrane (Nytran® N+, Schleicher & Schuell, Keene, N.H.) at 400 mA, 20 mV for 30 minutes. The membrane was then rinsed in 2 X SSC, blotted onto denaturation solution for five minutes, neutralized in 2 X SSC, then cross-linked damp in a UV crosslinker (Stratalinker®, Stratagene Cloning Systems) on automatic setting. The blot was hybridized to a PCR-generated AUG1 promoter probe using a commercially available kit (ECL™ kit, Amersham Corp., Arlington Heights, Ill.). Results indicated that the transforming DNA altered the structure of the AUG1 promoter DNA, consistant with a homologous integration event (FIG. 2).

Figure 3:
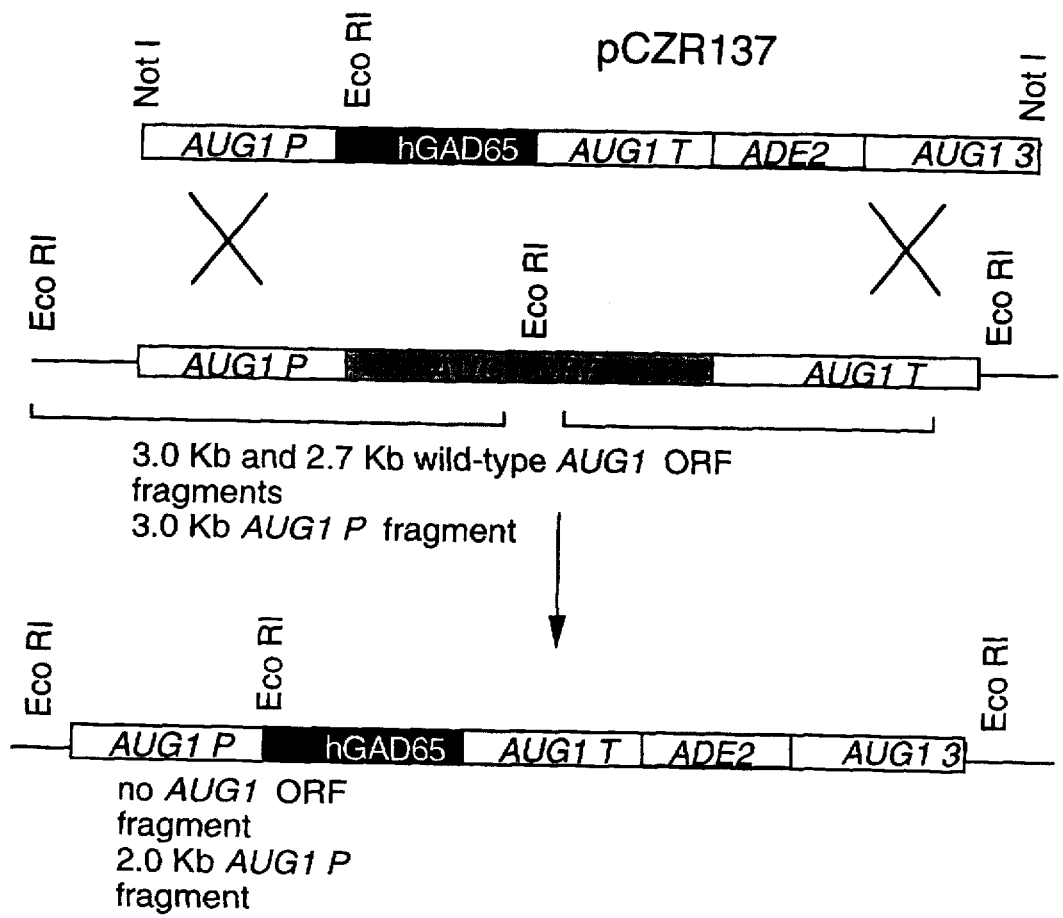
FIG. 3 is a schematic diagram of a recombination event between plasmid pCZR137 and *P. methanolica* genomic DNA.

In a second experiment, *P. methanolica* ade 2 strain #11 was transformed to Ade$^+$with Not I-digested pCZR137, a vector containing a human GAD65 cDNA between the AUG1 promoter and terminator (FIG. 3). Genomic DNA was prepared as described above from wild-type cells and a stable, white, Ade$^+$ transformant and digested with Eco RI. The digested DNA was separated by electrophoresis and blotted to a membrane. The blot was probed with a PCR-generated probe corresponding to either the AUG1 open reading frame or the AUG1 promoter. Results demonstrated that the AUG1 open reading frame DNA was absent from the transformant strain, and that the AUG1 promoter region had undergone a significant rearrangement. These results are consistent with a double recombination event (transplacement) between the transforming DNA and the host genome (FIG. 3).

Example 6

An AUG1 strain of *P. methanolica* is grown in high-density fermentation conditions. The fermentation vessel is charged with mineral salts by the addition of 57.8 g (NH$_4$)$_2$SO$_4$, 46.6 g KCl, 30.8 g MgSO$_4$.7H$_2$O, 8.6 g CaSO$_4$.2H$_2$O, 2.0 g NaCl, and 10 ml antifoam (PPG). H$_2$O is added to bring the volume to 2.5 L, and the solution is autoclaved 40 minutes. After cooling, 350 ml of 50% glucose, 250 ml 10 X trace elements (Table 4), 210 ml of 30% NaPhosphate, 25 ml 200 μg/ml biotin, and 250 ml cell inoculum are added. Cells are batch-fed glucose or glucose/methanol in three phases. In phase 1, the cells receive 0.4%/L/hour glucose (w/v final fermentation volume) for 25 hours using 750 g glucose, 110 g (NH$_4$)$_2$SO$_4$, and 278 ml 10 X trace elements per 1.5 liter. The cells are then given a transition feed of 0.2% glucose, 0.2% methanol/L/hour for 5 hours. The final glucose-supplemented methanol feed contains 0.1% glucose, 0.4% methanol/L/hr for 25 hours. Final biomass is about 300 g/L cell paste.

Example 7

For fermentation of a *P. methanolica* aug1Δ strain, the fermentation vessel is initially charged with mineral salts, glucose, phosphate, trace elements and biotin as disclosed in Example 6. 250 ml of cell inoculum is added. A glucose feed is prepared using 600 g glucose, 108 g (NH$_4$)$_2$SO$_4$, and 273 ml 10 X trace elements per 1.2 liter. The cells are batch-fed in three phases. In the first phase, the cells receive glucose for 12 to 25 hours at 0.4%/L/hour. The cells are then induced with a bolus addition of 1% methanol by weight and transitioned to methanol utilization with a mixed 0.2% glucose/0.1% methanol feed for 10 hours. In the third phase, a mixed feed of 0.2% glucose, 0.2% methanol is delivered for 15 hours.

Example 8

*P. methanolica* cells in which the AUG1 gene had been disrupted by insertion of a GAD65 expression construct retained the ability to grow on methanol, indicating that a second alcohol oxidase gene was present. The second gene, designated AUG2, was identified by PCR. Sequence analysis of the 5' coding region of the gene showed that the N-terminus of the encoded protein was similar to those of known alcohol oxidase genes.

Strain MC GAD8, a transformant that grew very poorly on minimal methanol broth, was used as a source for cloning the AUG2 gene. Genomic DNA was prepared from MC GAD8 and amplified with sense and antisense PCR primers specific for the AUG1 open reading frame (8784, SEQ ID NO:5; 8787, SEQ ID NO:6). A product identical in size to the AUG1 product but showing very low intensity on an analytical gel was obtained.

The putative AUG2 PCR product was digested with a battery of restriction enzymes. Partial digestion by Eco RI and Pvu I, and the presence of several Bgl II sites suggested that the DNA was contaminated with small amounts of AUG1. To remove the contaminating AUG1 DNA, the PCR mixture was cut with Eco RI and gel purified. Since the MC GAD 8 product did not appear to have an Eco RI site, it was unaffected. The resulting gel-purified DNA was reamplified and again analyzed by restriction digestion. The DNA gave a different restriction map from that of the AUG1 PCR product.

Southern blot analysis was performed on genomic DNA from MC GAD8 and wild-type cells using either AUG1 or AUG2 open reading frame PCR fragments as probes. The AUG2 probe hybridized at low stringency to the AUG1 locus and at both low and high stringency to a second locus. The AUG1 probe bound to both loci at low stringency, but bound predominantly to the AUG1 locus at high stringency. These data indicated that the new PCR product from MC GAD8 was similar to but distinct from AUG1. Sequence analysis showed an 83% identity between AUG1 and AUG2 gene products.

To clone the AUG2 genomic locus, PCR primers were designed from the original AUG2 PCR fragment. Primers 9885 (SEQ ID NO:7) and 9883 (SEQ ID NO:8) were used to screen a *P. methanolica* genomic library. A positive clone bank pool was then probed with the original MC GAD8 PCR product. Cells were plated on 10 plates at about 5000 colonies/plate and grown overnight, then the plates were overlayed with filter discs (Hybond-N, Amersham Corp., Arlington Heights, Ill.). Colonies were denatured, neutralized, and UV cross-linked. Bacterial debris was washed from the filters with 5X SSC, and the filters were again cross-linked. Blots were pre-hybridized in pairs at 42° C. for 1 hour in 25 ml hybridization buffer. Approximately 250 ng of probe was then added to each pair of filters. Hybridization was conducted at 42° C. for four hours. The blots were then washed in 500 ml of 0.1 X SSC, 6M urea, 0.4% SDS at 42° C. for 10 minutes, four times. The blots were then neutralized with 500 ml of 2 X SSC at room temperature for 5 minutes, two rinses. The blots were then immersed in 100 ml development reagent (ECL, Amersham Corp.).

Positive colonies were picked and amplified using PCR primers 9885 (SEQ ID NO:7) and 9883 (SEQ ID NO:8) to confirm their identity. Positive pools were streaked on plates, and single colonies were rescreened by PCR. One colony was selected for further analysis (restriction mapping and sequencing). A partial sequence of the AUG2 gene is shown in SEQ ID NO:9. As shown in SEQ ID NO:9, the AUG2 sequence begins at the HindIII site a nucleotide 91. Nucleotides upstream from this position are vector sequence. The coding sequence begins at nucleotide 170.

Disruption of the AUG2 gene had little effect on cell growth on methanol. Cells lacking both functional AUG1 and AUG2 gene products did not grow on methanol. Subsequent analysis showed that the AUG1 gene product is the only detectable alcohol oxidase in cells grown in a fermentor.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for preparing *Pichia methanolica* cells auxotrophic for adenine comprising:

(a) exposing *P. methanolica* cells to mutagenizing conditions;

(b) culturing the cells from step (a) in a rich medium to allow mutations to become established and replicated in at least a portion of said cells;

(c) culturing the cells from step (b) in a culture medium deficient in assimilable nitrogen to deplete cellular nitrogen stores;

(d) culturing the cells from step (c) in a defined culture medium comprising an inorganic nitrogen source and an amount of nystatin sufficient to kill growing *P. methanolica* cells to select for cells auxotrophic for adenine; and (e) culturing the selected cells from step (d) in a rich culture medium.

2. A method according to claim 1 wherein the selected cells from step (e) are replica plated to a defined medium lacking adenine to confirm the presence of an auxotrophic mutation for adenine.

3. A method according to claim 1 wherein the selected cells are deficient in phosphoribosyl-5-aminoimidazole carboxylase.

4. A method according to claim 1 wherein the defined culture medium contains 2 mg/L nystatin.

5. A method according to claim 1 wherein the mutagenizing conditions comprise exposure to ultraviolet light.

6. A method according to claim 1 wherein the mutagenizing conditions comprise exposure to a chemical mutagen.

7. A method according to claim 1 wherein the inorganic nitrogen source comprises ammonium ions.

8. A method according to claim 7 wherein the inorganic nitrogen source is ammonium sulfate.

* * * * *